US012685710B2

(12) United States Patent
Aguilar-Galindo et al.

(10) Patent No.: US 12,685,710 B2
(45) Date of Patent: Jul. 21, 2026

(54) ADMINISTRATION OF CICLOPIROX WITH NO ADVERSAL GASTROINTESTINAL TOXICITY

(71) Applicants: ATLAS MOLECULAR PHARMA, S.L., Derio-Bizkaia (ES); ASOCIACIÓN CENTRO DE INVESTIGACIÓN COOPERATIVA EN BIOCIENCIAS-CIC bioGUNE, Derio-Vizcaya (ES)

(72) Inventors: Oscar Millet Aguilar-Galindo, Derio-Vizcaya (ES); Joaquín Castilla Castrillòn, Derio-Vizcaya (ES); Ganeko Bernardo-Seisdedos, Derio-Bizkaia (ES); Jorge Moreno Charco, Derio-Bizkaia (ES)

(73) Assignees: ATLAS MOLECULAR PHARMA, S.L., Derio-Bizkai (ES); ASOCIACIÓN CENTRO DE INVESTIGACIÓN COOPERATIVA EN, Derio-Vizcay (ES)

( * ) Notice: Subject to any disclaimer, the term of this patent is extended or adjusted under 35 U.S.C. 154(b) by 255 days.

(21) Appl. No.: 18/713,898

(22) PCT Filed: Dec. 9, 2022

(86) PCT No.: PCT/EP2022/085126
§ 371 (c)(1),
(2) Date: May 28, 2024

(87) PCT Pub. No.: WO2023/105031
PCT Pub. Date: Jun. 15, 2023

(65) Prior Publication Data

US 2025/0025416 A1 Jan. 23, 2025

(30) Foreign Application Priority Data

Dec. 9, 2021 (EP) .................................... 21383119

(51) Int. Cl.

| | |
|---|---|
| ***A61K 9/08*** | (2006.01) |
| ***A61K 9/00*** | (2006.01) |
| ***A61K 31/4418*** | (2006.01) |
| ***A61K 47/22*** | (2006.01) |
| ***A61K 47/36*** | (2006.01) |

(52) U.S. Cl.
CPC .............. *A61K 9/08* (2013.01); *A61K 9/0095* (2013.01); *A61K 31/4418* (2013.01); *A61K 47/22* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 2,680,749 | A | 6/1954 | Cawley et al. |
| 3,883,545 | A | 5/1975 | Lohaus et al. |

FOREIGN PATENT DOCUMENTS

| | | | |
|---|---|---|---|
| CN | 103191110 | A | 7/2013 |
| CN | 105343071 | A | 2/2016 |
| CN | 108926562 | A | 12/2018 |
| EP | 3315129 | A1 | 5/2018 |
| WO | WO 2001/87355 | | 11/2001 |
| WO | WO 2012/075396 | | 6/2012 |
| WO | WO 2016/077346 | | 5/2016 |

OTHER PUBLICATIONS

Al-Zubaydi et al., Breast intraductal nanoformulations for treating ductal carcinoma in situ I: Exploring metal-ion complexation to slow ciclopirox release, enhance mammary persistence and efficacy. J Control Release. Jul. 10, 2020:323:71-82.

Al-Zubaydi et al., Breast intraductal nanoformulations for treating ductal carcinoma in situ II: Dose de-escalation using a slow releasing/slow bioconverting prodrug strategy. Drug Deliv Transl Res. Jan. 2022;12(1):240-256.

Barot et al., Design, synthesis and docking studies of some novel (R)-2-(4'-chlorophenyl)-3-(4'-nitrophenyl)-1,2,3,5-tetrahydrobenzo[4,5] imidazo [1,2-c]pyrimidin-4-ol derivatives as antitubercular agents. Eur J Med Chem. Aug. 18, 2014:83:245-55.

Berardo-Seisdedos et al., Improving the Pharmacological Properties of Ciclopirox for its use in Congenital Erythropoietic Porphyria. J Pers Med. May 28, 2021;11(6):485. 11 pages.

Builders et al., Preparation and evaluation of mucinated sodium alginate microparticles for oral delivery of insulin. Eur J Pharm Biopharm. Nov. 2008;70(3):777-83.

Luiz et al., The use of TPGS in drug delivery systems to overcome biological barriers. European Polymer Journal. Jan. 2021, 142, 110129, 15 pages.

Manabe et al., Efficacy of adding sodium alginate to omeprazole in patients with nonerosive reflux disease: a randomized clinical trial. Dis Esophagus. Jul. 2012;25(5):373-80.

Minden et al., Oral ciclopirox olamine displays biological activity in a phase I study in patients with advanced hematologic malignancies. Am J Hematol. Apr. 2014;89(4):363-8.

Pawar et al., Alginate derivatization: a review of chemistry, properties and applications. Biomaterials. Apr. 2012;33(11):3279-305.

Qi et al., Ciclopirox activates PERK-dependent endoplasmic reticulum stress to drive cell death in colorectal cancer. Cell Death Dis. Jul. 27, 2020;11(7):582. 16 pages.

Radadiya et al., Ciclopirox olamine induces ferritinophagy and reduces cyst burden in polycystic kidney disease. JCI Insight. Mar. 30, 2021;6(8):e141299. 15 pages.

Severino et al., Alginate Nanoparticles for Drug Delivery and Targeting. Curr Pharm Des. 2019;25(11):1312-1334.

(Continued)

*Primary Examiner* — Nannette Holloman

(74) *Attorney, Agent, or Firm* — Casimir Jones, S.C.; Tristan A. Fuierer

(57) ABSTRACT

The present invention relates to an oral composition of ciclopirox or a derivate thereof which do not exhibit gastrointestinal toxicity and comprises a therapeutically effective amount of ciclopirox, tocopherol and alginate or their derivates.

18 Claims, 4 Drawing Sheets

(56) References Cited

OTHER PUBLICATIONS

Urquiza et al., Repurposing ciclopirox as a pharmacological chaperone in a model of congenital erythropoietic porphyria. Sci Transl Med. Sep. 19, 2018;10(459):eaat7467. 10 pages.
Weir et al., Fosciclopirox suppresses growth of high-grade urothelial cancer by targeting the γ-secretase complex. Cell Death Dis. May 31, 2021;12(6):562. 20 pages.
Weir et al., Preclinical Pharmacokinetics of Fosciclopirox, a Novel Treatment of Urothelial Cancers, in Rats and Dogs. J Pharmacol Exp Ther. Aug. 2019;370(2):148-159.
Zhang et al., A colon targeted drug delivery system based on alginate modificated graphene oxide for colorectal liver metastasis. Mater Sci Eng C Mater Biol Appl. Oct. 1, 2017:79:185-190.

A B C

ADMINISTRATION OF CICLOPIROX WITH NO ADVERSAL GASTROINTESTINAL TOXICITY

CROSS-REFERENCE TO RELATED APPLICATIONS

This application is filed under the provisions of 35 U.S.C. § 371 and claims the priority of International Patent Application No. PCT/EP2022/085126 filed on 9 Dec. 2022 entitled "A FORMULATION FOR AN EFFECTIVE ORAL ADMINISTRATION OF CICLOPIROX WITH NO ADVERSAL GASTROINTESTINAL TOXICITY" in the name of Oscar MILLET AGUILAR-GALINDO, et al., which claims priority to European Patent Application No. 21383119.1, filed on 9 Dec. 2021, both of which are hereby incorporated by reference herein in their entirety.

FIELD OF THE INVENTION

A method for the oral administration of ciclopirox (CPX) and ciclopirox derivates is provided, that prevents gastrointestinal toxicity. The formulae provided enables the oral administration of CPX and their derivates in a therapeutically effective amount without the gastrointestinal toxicity attributed to the active species.

BACKGROUND OF THE INVENTION

Deficient pharmacological properties and associated toxicity constitute the main sources for the failure of clinical trials using drugs that have proven active in preclinical studies. To be safe, a drug must be utterly eliminated from the body, ideally not long after the activity's window timeframe and with no reported toxic effects in the organism. To that end, the drug catabolismpharmacokinetics, PK) has to be harmonized with the pharmacological effect of the drug (pharmacodynamics). Drug toxicity refers to the level of damage that a compound can cause to an organism. The toxic effects of a drug are dose-dependent and will ultimately limit the maximum dose that can be administered for an active species. Sometimes it is possible to expand the therapeutic window of a drug by ameliorating or even suppressing the toxic effects of the given drug, when administered with the correct formulation.

The molecule 6-cyclohexyl-1-hydroxy-4-methylpyridin-2-one known as ciclopirox (CPX) or the olamine salt form of ciclopirox (CPX-O) are commercially available topical antimycotic agents with additional antibacterial and anti-inflammatory activities. Ciclopirox is approved in the US for different indications and by different holders: as 1% cream or lotion and as 0.77% gel for the treatment of fungal skin infections; as 1% shampoo to treat seborrheic dermatitis; and as 8% nail lacquer for the treatment of onychomycosis. In all cases, the route of administration is topic. Additionally, oral administration of CPX is currently under investigation to evaluate its use in rare diseases such as congenital erythropoietic porphyria[1] (EP3315129A1), other hematologic malignancies[2], melanoma (CN103191110A), urothelial cancer[3,4], breast intraductal carcinoma[5,6], bladder cancer (WO2016077346A1), colorectal cancer[7], epilepsy (CN105343071A) and polycystic kidney disease[8]. Yet, oral administration of CPX is limited due to the significant first-pass effect that lowers its systemic bioavailability.

More importantly, despite delivery through oral administration would be beneficial for all these potential applications, the oral administration of CPX is associated with gastrointestinal (GI) toxicity. Specifically, a Phase I study (Trial registration ID: NCT00990587) was performed with ciclopirox olamine administered orally (using OraSweet formulation) to patients with hematological malignancies[2]. In the Phase I clinical trial performed by Minden et al., grade 3 GI dose limiting toxicity (DLTs) and bowel inflammation were observed in 3/4 patients in the cohort receiving 80 $mg/m^2$ (2.2 mg/kg) 4 times daily. Overall, once-daily dosing of ciclopirox olamine up to and including 40 $mg/m^2$ (1.1 mg/kg) was well tolerated. However, grade 1 and 2 GI toxicities possibly related to the study drug were observed in six (31.6%) patients treated once daily with doses greater than 5 $mg/m^2$ (0.13 mg/kg).

Some prodrug forms have been proposed to improve the systemic availability of CPX. Specifically, a phosphoryl-oxo-methylene group can be chemically conjugated to the given hydroxyl group to yield a stable entity[9]. Such strategy effectively suppressed GI toxicity in WT mice and in a mouse model of the congenital erythropoietic porphyria disease. Yet, in terms of activity, phosphorylation of CPX yielded good results in CEP cellular models but showed no efficacy when administered to the CEP mouse model[10].

Altogether, there is still a great need of providing proper formulations for CPX and/or derivatives thereof such as CPX-O that enable their therapeutic use in oral administration.

SUMMARY OF THE INVENTION

The present invention solves one or more of the aforementioned needs by the provision of a new composition for the oral administration of ciclopirox (CPX) and ciclopirox derivates. Advantageously, the composition provided is devoid of the problems of gastrointestinal toxicity and systemic bioavailability observed in the prior art for this active ingredient.

Thus, the present invention relates to an oral pharmaceutical composition comprising:

- a therapeutically effective amount of ciclopirox or a pharmaceutically acceptable salt, solvate or prodrug thereof,
- tocopherol or a pharmaceutically acceptable salt, ester or ether thereof, and
- alginate or a pharmaceutically acceptable salt, ester or ether thereof.

Additional excipients or materials may be also included in the pharmaceutical composition of the invention.

A further aspect is the pharmaceutical composition of the invention as defined above for use in medicine, and more particularly in the treatment and/or prevention of a disease known to be treatable and/or preventable by ciclopirox and its derivates including, but not limited to, hematologic malignancies, cancers, fungal and bacterial infections, inflammatory diseases, epilepsy and polycystic kidney disease. Also is disclosed a method for the treatment and/or prevention in a subject of a disease known to be treatable and/or preventable by ciclopirox and its derivates, said method comprising the administration of the pharmaceutical composition of the invention as defined above to said subject. In a preferred embodiment, said subject is a human being.

These aspects and preferred embodiments thereof are additionally also defined hereinafter in the detailed description and in the claims.

BRIEF DESCRIPTION OF THE DRAWINGS

To better understand the invention, its objects and advantages, the following figures are attached to the specification in which the following is depicted.

DETAILED DESCRIPTION OF THE INVENTION

Figure 1:
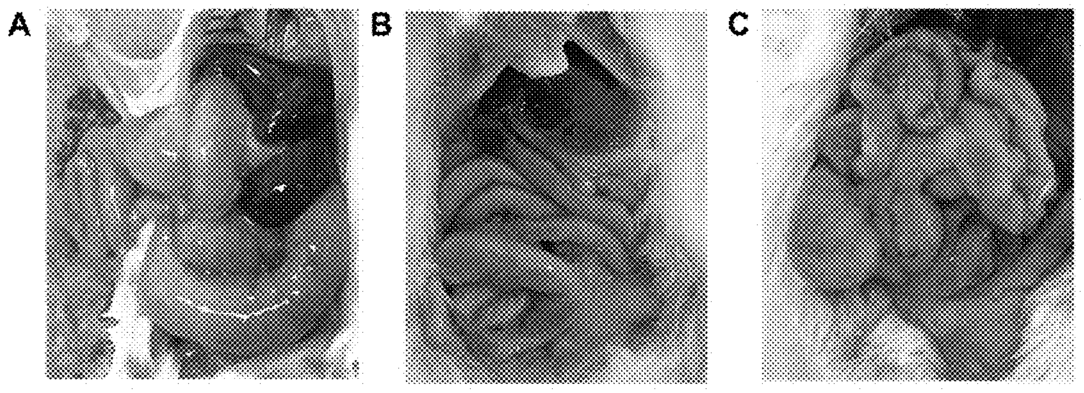
FIG. 1: Gastrointestinal effect of ciclopirox formulations Abdominal views of representative mice that have been treated with 25 mg of ciclopirox (gavage) (A), 25 mg/kg of ciclopirox olamine (B) and 100 mg/kg of ciclopirox olamine (C), both formulated as an oral solution identified as ATL-001 according to the present invention, with tocofersolan and sodium alginate and the rest of excipients shown in Table 1.

The present invention refers to a galenic formulation that improves CPX gastrointestinal tolerance after oral administration. The pharmaceutical formulation is based on the combination of the following ingredients: CPX or a CPX derivate, a tocopherol compound, and an alginate compound. CPX or a derivate thereof acts as the active ingredient while the tocopherol and the alginate compounds may be regarded as pharmaceutically acceptable excipients.

Specifically, the present invention relates the combination of a tocopherol compound and an alginate compound to overcome CPX GI toxicity. Other optional excipients may be added to the formulation but they do not contribute to the CPX GI toxicity, as it will be demonstrated in the examples. Additionally, it has been found that the composition of the invention may be pharmacokinetically bioequivalent to the reference product, i.e. oral administration of the active ingredient alone, and may also exhibit a suitable stability.

The compound ciclopirox was disclosed for the first time in the 1970s, in U.S. Pat. No. 3,883,545, where it was described as exhibiting antimycotic properties[11]. The chemical name for ciclopirox is 6-cyclohexyl-1-hydroxy-4-methyl-2 (1H)-pyridone, with the molecular formula $C_{12}H_{17}NO_2$ and a molecular weight of 207.27. The CAS Registry Number is [29342-05-0]. The chemical structure is depicted below in Scheme 1:

Scheme 1 Ciclopirox

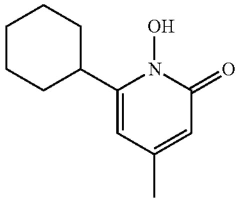

The present invention also contemplates ciclopirox derivates, namely all pharmaceutically acceptable salts, solvates and prodrugs of ciclopirox. For instance, ciclopirox can be for example ciclopirox olamine (CAS Registry Number [41621-49-2]), which comprises 6-cyclohexyl-1-hydroxy-4-methyl-2 (1H)-pyridone with 2-aminoethanol in a 1:1 ratio.

The term "salt" must be understood as any form of a compound used according to this invention in which said compound is in ionic form or is charged and coupled to a counterion (a cation or anion).

Salts of ciclopirox may preferably be base addition salts or metallic salts, and they can be synthesized from the parent compound by conventional chemical methods. Examples of the alkali addition salts include inorganic salts such as, for example, ammonium, and organic alkali salts such as, for example, ethylenediamine, ethanolamine, triethanolamine, glutamine and basic amino acids salts. Examples of the metallic salts include, for example, sodium, potassium, calcium, magnesium, aluminium, and lithium salts. According to a particular embodiment, the salt of ciclopirox is a salt of alkali metals (for example of sodium or potassium); an ammonium salt; a primary amine salt (as for example $C_1$-$C_8$ alkyl amine); a secondary amine salt (as for example $C_1$-$C_8$ dialkyl amine); a tertiary amines salt (as for example $C_1$-$C_8$ trialkyl amine); a diamine salt; an alkanolamine salt (as for example $C_1$-$C_8$ alkanolamine or $C_1$-$C_8$ dialkanolamine or $C_1$-$C_8$ trialkanolamine); a $C_1$-$C_8$ dialkyl $C_1$-$C_8$ alkanolamine; or a $C_1$-$C_8$ alkyl $C_1$-$C_8$ dialkanolamine. A preferred ciclopirox salt is ciclopirox olamine.

The term "solvate" according to this invention is to be understood as meaning any form of the compound according to the invention in which this compound has attached to it via non-covalent binding another molecule (most likely a polar solvent) especially including hydrates and alcoholates, e.g. methanolate. Methods of solvation are generally known within the art.

The term "prodrug" is used in its broadest sense and encompasses those derivatives that are converted in vivo to ciclopirox. Such derivatives would readily occur to those skilled in the art, and include without limitation, the following derivatives of CPX: ethers, such as POM (phosphoryl-oxo-methylene) ethers as those described in WO2012075396 A2[9]; esters, including carboxylic acid esters, amino acid esters, phosphate esters, metal salts sulfonate esters; carbamates; and amides. Examples of well-known methods of producing a prodrug of a given acting compound are known to those skilled in the art 30 and can be found e.g. in Krogsgaard-Larsen et al. "Textbook of Drug design and Discovery" Taylor & Francis (April 2002). The chemical structure of a ciclopirox-POM prodrug is depicted below in Scheme 2:

Scheme 2 Ciclopirox-POM produg

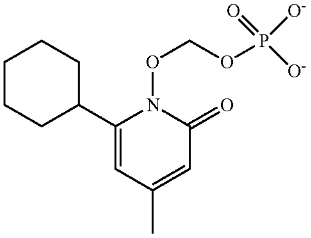

Tocopherols are a class of compounds that exhibit vitamin E activity and which exist in four forms designated as a (alpha), β (beta), γ (gamma) and δ (delta), all of which are included in the context of the present invention as well as derivates and combinations thereof. In one particular embodiment, the form of the tocopherol compound is α-tocopherol or β-tocopherol, preferably α-tocopherol. Tocopherols also include without limitation stereoisomers (e.g., + and − stereoisomers and racemic mixtures (+/−) of an α-, β-, γ-, or δ-tocopherol).

Tocopherol derivates include for instance salts, esters (e.g. carboxylic acid esters, phosphoesters and sulfate esters) or ethers thereof. In a particular embodiment, the tocopherol compound is α-tocopherol or an ester thereof. Suitable tocopherol esters (tocopheryl acid esters) include both esters of tocopherol with monocarboxylic acids and dicarboxylic acids or other polybasic acids as well as with phosphoric and sulfuric acid.

In certain embodiments, the ester of tocopherol is an ester with a $C_1$-$C_{22}$ mono- or dicarboxylic acid.

In certain embodiments, the tocopherol ester may be selected for instance from the group consisting of: tocopherol acetates, tocopherol propionates (e.g. n- and iso-propionates), tocopherol butyrates (e.g. n- and iso-butyrates), tocopherol allophanates, tocopherol enanthates, tocopherol myristates, tocopherol palmitates, tocopherol stearates, tocopherol linoleates, tocopherol behenates, tocopherol nicotinates, tocopherol phosphates, tocopherol sulfates, tocopherol succinates, tocopherol citraconates, tocopherol α-methylcitraconates, tocopherol itaconates, tocopherol maleates, tocopherol glutaconates and tocopherol phthalates as well as the polyethylene glycol esters of the foregoing dicarboxylic acid esters of tocopherol.

In certain embodiments, the tocopherol is selected from the group consisting of β-tocopherols, sorbitan esters of tocopherols, d-α-tocopherol, d,l-α-tocopherol, d-α-tocopherol acetate, d,l-α-tocopherol acetate, d-α-tocopherol succinate, d,l-α-tocopherol succinate, d-α-tocopherol nicotinate, d,l-α-tocopherol nicotinate, tocopherylpolyethylene glycol succinate such as d-α-tocopherylpolyethylene glycol succinate or d,l-α-tocopherylpolyethylene glycol succinate.

In certain embodiments, the tocopherol is selected from a polyethylene glycol ester of a dicarboxylic acid ester of tocopherol (e.g. PEG esters of tocopherol succinates, tocopherol citraconates, tocopherol α-methylcitraconates, tocopherol itaconates, tocopherol maleates, tocopherol glutaconates and tocopherol phthalates), wherein the PEG moiety has a molecular weight in the range from 200 to 6000, e.g. 200 to 1500.

In certain embodiments, the tocopherol is a tocopherylpolyethylene glycol succinate, which preferably is selected from the group consisting of:

d-α-tocopherylpolyethylene glycol 200 succinate, d,l-α-tocopherylpolyethylene glycol 200 succinate, d-α-tocopherylpolyethylene glycol 300 succinate, d,l-α-tocopherylpolyethylene glycol 300 succinate, d-α-tocopherylpolyethylene glycol 400 succinate, d,l-α-tocopherylpolyethylene glycol 400 succinate, d-α-tocopherylpolyethylene glycol 500 succinate, d,l-α-tocopherylpolyethylene glycol 500 succinate, d-α-tocopherylpolyethylene glycol succinate, d,l-α-600 tocopherylpolyethylene glycol 600 succinate, d-α-tocopherylpolyethylene glycol 700 succinate, d,l-α-tocopherylpolyethylene glycol 700 succinate, d-α-tocopherylpolyethylene glycol 800 succinate, d,l-α-tocopherylpolyethylene glycol 800 succinate, d-α-tocopherylpolyethylene glycol 800 succinate, d,l-α-tocopherylpolyethylene glycol 800 succinate, d-α-tocopherylpolyethylene glycol 900 succinate, d,l-α-tocopherylpolyethylene glycol 900 succinate, d-α-tocopherylpolyethylene glycol 1000 succinate, d,l-α-tocopherylpolyethylene glycol 1000 succinate, d-α-tocopherylpolyethylene glycol 1100 succinate, d,l-α-tocopherylpolyethylene glycol 1100 succinate, d-α-tocopherylpolyethylene glycol 1200 succinate, d, I-α-tocopherylpolyethylene glycol 1200 succinate, d-α-tocopherylpolyethylene glycol 1300 succinate, d,l-α-tocopherylpolyethylene glycol 1300 succinate, d-α-tocopherylpolyethylene glycol 1400 succinate, d,l-α-tocopherylpolyethylene glycol 1400 succinate, d-α-tocopherylpolyethylene glycol 1450 succinate, d,l-α-tocopherylpolyethylene glycol 1450 succinate, d-α-tocopherylpolyethylene glycol 1500 succinate, d,l-α-tocopherylpolyethylene glycol 1500 succinate, d-α-tocopherylpolyethylene glycol 1600 succinate, d,l-α-tocopherylpolyethylene glycol 1600 succinate, and d-α-tocopherylpolyethylene glycol 1700 succinate and d,l-α-tocopherylpolyethylene glycol 1700 succinate.

Tocopherol derivates including PEG tocopherol esters are widely known in the state of the art[12].

Preferred tocopherols for use according to the present invention are d-α-tocopherylpolyethylene glycol 1000 succinate (in the following denoted tocofersolan, vitamin E TPGS or simply TPGS) or d, I-α-tocopherylpolyethylene glycol 1000 succinate.

Tocofersolan (also known as TPGS or Vitamin E TPGS) is a water-soluble amphipathic formulation of d-α-tocopherol succinate linked to polyethylene glycol 1000 though a succinate linker. The chemical name of the molecule is 1-O-(2-hydroxyethyl) 4-O-[2,5,7,8-tetramethyl-2-(4,8,12-trimethyltridecyl)-3,4-dihydrochromen-6-yl] butanedioate with a molecular formula $C_{35}H_{58}O_6$ and a molecular weight of 574.8. The CAS Registry Number is [30999-06-5|9002-96-4]. The chemical structure is depicted below in Scheme 3:

Scheme 3 Tocofersolan

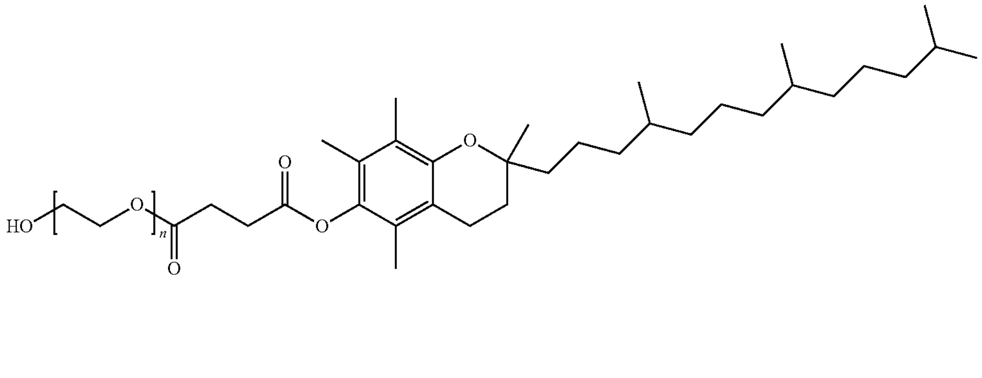

TPGS has an amphiphilic structure composed by a lipophilic tail of vitamin E and a hydrophilic PEG head with a low critical micelle concentration (CMC) of 0.02% w/w. The hydrophile-lipophile balance value is 13.2. TPGS is a non-ionic surfactant that has proven to be a cell permeation enhancer[13]. So far, the present work presents for the first time the combination of CPX with this excipient to cope with the gastrointestinal toxicity. TPGS is a biocompatible and biodegradable substance that has been approved by FDA, EMA, as a safe pharmaceutical adjuvant. There is a monograph for Vitamin E TPGS in the current United States Pharmacopeia/National Formulary (USP/NF).

Alginate (alginic acid) is a FDA approved hydrophilic and anionic polysaccharide composed by L-glucuronic and D-mannuronic acid residues connected via 1,4-glycosidic linker. The chemical name of this molecule is 3-(6-carboxy-3,4-dihydroxy-5-phosphanyloxan-2-yl)oxy-4,5-dihydroxy-6-phosphanyloxyoxane-2-carboxylic acid. It has a MW of 418.23 and a molecular formula of $C_{12}H_{20}O_{12}P_2$ per monomer. The CAS Registry Number is [9005-32-7]. The chemical structure is depicted below in Scheme 4:

Scheme 4 Alginate

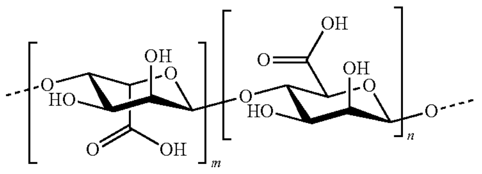

Alginate has been widely used in biomedical science due to its biocompatibility, biodegradability, and no-immunogenicity. Alginate is water soluble that could form nanoparticles and/or mild gels[14]. Alginate nanoparticles have been applied as a drug delivery system for molecules such as DNA, peptides, antigens and proteins in many diseases such as diabetes[15], nonerosive reflux disease[16], tuberculosis[17], colorectal liver metastasis[18] among others.

A large number of alginate derivates have been described[19], including salts, esters (carboxylic acid esters, phosphoesters and sulfate esters) and ethers thereof, all of which are included in the context of the present invention as well as combinations thereof.

According to some embodiments, the alginate is selected from alginic acid, an alginate salt and an ester thereof.

Examples of alginate salts within the scope of present invention include, but are not limited to, base addition salts (for example, ammonium, and organic alkali salts such as ethylenediamine, ethanolamine, triethanolamine, glutamine and basic amino acids salts) or metallic salts (for example, sodium, potassium, calcium, magnesium, aluminium, and lithium salts). In certain embodiments, the alginate salt is selected from the group consisting of alkali metallic salts of alginic acid (e.g. sodium, potassium) alkaline earth metallic salts of alginic acid (e.g. calcium, magnesium), zinc salt of alginic acid, and ammonium salt of alginic acid. In certain embodiments, the alginate salt is selected from the group consisting of alkali metallic salts of alginic acid, the ammonium salt of alginic acid, and the magnesium salt of alginic acid. More preferably, the alginate salt is sodium alginate.

In certain embodiments, the alginate used in the present invention is an esterified alginate, such as a $C_2$-$C_5$-diol ester of alginate or a $C_3$-$C_5$-triol ester of alginate. As used herein, an "esterified alginate" or "alginate ester" means an alginic acid in which some of the carboxyl groups of the alginic acid are esterified. The remainder of the carboxylic acid groups are optionally neutralized (partially or completely) as pharmaceutically acceptable salts. For example, propylene glycol alginate is an ester of alginic acid in which some of the carboxyl groups are esterified with propylene glycol, and the remainder of the carboxylic acid groups are optionally neutralized (partially or completely) as pharmaceutically acceptable salts. Alkylene glycol alginates are most generally available as propylene glycol esters of alginic acid in which from 30% to 90% of the carboxyl groups have been esterified with propylene glycol, the remaining groups being either free or neutralized with a base. More preferably, the alginate ester is ethylene glycol alginate, trimethylene glycol alginate, propylene glycol alginate, butylene glycol alginate, isobutylene glycol alginate, pentylene glycol alginate or glycerol alginate and mixtures thereof. Propylene glycol alginate (PGA) is even more preferred.

The pharmaceutical compositions provided herein for oral administration can be provided in solid, semisolid, or liquid form. In certain embodiments, the composition is formulated as a semisolid or a liquid. Alternatively, the composition may be formulated as a solid (e.g. effervescent or non-effervescent powders or granules) which may be dissolved or mixed with a liquid or solvent so as to obtain a semisolid or a liquid composition for final use. Alternatively, the composition may be formulated as a semisolid which may be dissolved or mixed with a liquid or solvent so as to obtain a liquid composition for final use. Suitable semisolid and liquid oral compositions include, but are not limited to, oral mists, solutions, emulsions, suspensions, elixirs, and syrups. In a particular embodiment, the composition of the invention is a solution.

The term "composition", "pharmaceutical composition", "formulation", "pharmaceutical formulation", "galenic formulation", "dosage form" and the like are used herein synonymously.

Besides the tocoferol and the alginate excipients, the compositions of the invention may further comprise one or more additional pharmaceutically acceptable excipients known to those skilled in the art. The selection of appropriate excipients and the amounts to be used will depend, in part, on the physical qualities desired for the formulation (viscosity, tongue feel, etc.).

By "pharmaceutically acceptable" is meant herein a material that is not biologically or otherwise undesirable, i. e., the material may be incorporated into a pharmaceutical composition administered to a patient without causing any undesirable biological effects or interacting in a deleterious manner with any of the other components of the composition in which it is contained. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "excipient" refers to constituent of a medicine other than the active substance, added in the formulation for a specific purpose (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins).

Exemplary excipients include, but are not limited to, binders, fillers, diluents, disintegrants, wetting agents, lubricants, glidants, buffering agents, coloring agents, flavoring agents, sweetening agents, preservatives, emulsifying agents, suspending and dispersing agents, organic acids and a source of carbon dioxide. Some excipients can serve multiple purposes.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof.

Suitable fillers or bulky agents include, but are not limited to, talc, calcium carbonate, microcrystalline cellulose, powdered cellulose, dextrates, kaolin, mannitol, silicic acid, sorbitol, starch, pre-gelatinized starch, and mixtures thereof.

Suitable diluents include, but are not limited to, dicalcium phosphate, calcium sulfate, lactose, sorbitol, sucrose, inositol, cellulose, kaolin, mannitol, sodium chloride, dry starch, powdered sugar, and mixtures thereof.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof.

Suitable wetting agents include, but are not limited to, propylene glycol monostearate, sorbitan monooleate, diethylene glycol monolaurate, polyoxyethylene lauryl ether, and mixtures thereof.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures thereof.

Suitable glidants include, but are not limited to, colloidal silicon dioxide, CAB-O-SIL® (Cabot Co. of Boston, MA), asbestos-free talc, and mixtures thereof.

Suitable buffering agents include, but are not limited to, citric acid, disodium hydrogen phosphate, glycine, hydrochloric acid, glacial acetic acid, sodium acetate trihydrate, trisodium citrate, potassium chloride, hydroxymethyl aminomethane, sodium hydroxide, carbonate, bicarbonate and mixtures thereof.

Suitable coloring agents or colorants include, but are not limited to, erythrosine, any of the approved, certified, water soluble FD And C dyes, and water insoluble FD And C dyes suspended on alumina hydrate, and color lakes and mixtures thereof. A color lake is the combination by adsorption of a water-soluble dye to a hydrous oxide of a heavy metal, resulting in an insoluble form of the dye. In certain embodiments, the composition of the invention comprises at least one colorant, which preferably is erythrosine.

Suitable flavoring agents or flavours include, but are not limited to, natural flavors extracted from plants, such as fruits (orange, peach, pear, peppermint, pineapple, cranberry, grape, grapefruit, guava, hop, lemon, lime, malt, molasses, mixed berry, raspberry, rose, vanilla, wintergreen, spearmint, strawberry, etc.) and synthetic compounds or blends of compounds which produce a pleasant taste sensation, such as strawberry aldehyde, peppermint and methyl salicylate, and mixtures thereof. In certain embodiments, the composition of the invention comprises at least one flavour, which preferably is strawberry aldehyde.

Suitable sweetening agents or sweeteners include, but are not limited to, natural and artificial sweeteners such as glucose, fructose, sucrose, xylitol, sucralose, maltitol, lactitol, sorbitol, erythritol, trehalose, lactose, mannitol, syrups, glycerin, maltodextrin, polydextrose, saccharin and aspartame, and mixtures thereof.

Suitable preservatives include, but are not limited to, glycerin, potassium sorbate, sorbic acid, methyl and propylparaben, benzoic acid, sodium benzoate, benzyl alcohol and mixtures thereof. In certain embodiments, the composition of the invention comprises at least one preservative, which preferably is an antimicrobial or bacteriostatic preservative such as benzyl alcohol.

Suitable emulsifying agents include, but are not limited to, gelatin, acacia, tragacanth, polyoxyethylene sorbitan monooleate bentonite, and surfactants, such as (TWEEN® 20), polyoxyethylene sorbitan monooleate 80 (TWEEN® 80), triethanolamine oleate, and mixtures thereof.

Suitable suspending and dispersing agents include, but are not limited to, sodium carboxymethylcellulose, pectin, tragacanth, Veegum, acacia, sodium carbomethylcellulose, hydroxypropyl methylcellulose, polyvinylpyrrolidone, and mixtures thereof.

The pharmaceutical compositions provided herein for oral administration can be provided in solid dosage forms, such as non-effervescent or effervescent, granules and powders, to be reconstituted into a semisolid or liquid dosage form. Pharmaceutically acceptable excipients used in the effervescent granules or powders may include organic acids and a source of carbon dioxide. Organic acids include for instance citric and tartaric acid. Sources of carbon dioxide include for instance sodium bicarbonate and sodium carbonate.

The pharmaceutical compositions provided herein for oral administration can be provided in liquid and semisolid dosage forms, including oral mists, solutions, emulsions, suspensions, elixirs, and syrups. Oral mists or oral sprays are liquids that you aerosol in your mouth. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, and emulsifying agent. Suspensions may include a pharmaceutically acceptable suspending agent. Solutions may be aqueous, alcoholic, or hydroalcoholic. For instance, aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose.

The pharmaceutical compositions provided herein generally comprise a solvent or are dissolved or mixed with a solvent before use, i.e. for their oral administration. In certain embodiments, the pharmaceutical composition of the invention comprises water as solvent, preferably as the sole solvent, but, as noted above, non-aqueous solvents are also contemplated as well as combinations of water and one or more non-aqueous solvents. Non-aqueous solvents include alcohols and oils and other liquids such as ethyl alcohol, sorbitol, silicone oil, vegetable oil, glycerin, hydrogenated vegetable oil, lecithin, beeswax, tochopherols, polyethylene glycols (e.g., PEG 200, 300, 400 or 600), polyoxyethylene-polyoxypropylene copolymers (poloxamers), propylene glycol, Miglyol® 812 (neutral oil, triglycerides of medium chain fatty acids), omega oil, soybean oil, canola oil, sunflower oil, macadamia oil, peanut oil, grapeseed oil, pumpkin seed oil, linseed oil, flaxseed oil, olive oil, maize oil, safflower oil, sesame oil, pine kernel oil, conjugated linoleic acid, almond oil, peach kernel oil, apricot kernel oil, walnut oil, rapeseed oil, raspberry seed oil, bilberry seed oil, cranberry seed oil, pomegranate seed oil and other fruit seed oils, seabuckthorn oil, chia oil, perilla oil, diaglycerol (DAG) oil, vegetable derived sources of omega 3, fermented sources of eicosapentaenoic acid (EPA), fermented sources of docosahexaenoic acid (DHA), fermented sources of a combination of EPA, DHA and other omega 3s, including fish oil and hill oil, sources of gamma-linolenic acid (GLA) or stearidonic acid (SA), fractionated coconut oil, and combinations thereof. Sources of DHA, EPA and alpha-linoleic acid (ALA) include, but are not limited to, fish oils, yeasts or other microorganisms or monocellular sources and vegetable oils, primarily flaxseed, soy, and canola. Sources of GLA include, but are not limited to, evening primrose oil, blackcurrent seed oil, borage oil, and echium oil.

In certain embodiments, the pharmaceutical composition of the invention further comprises benzyl alcohol. In certain embodiments, the pharmaceutical composition of the invention further comprises erythrosine. In certain embodiments, the pharmaceutical composition of the invention further comprises strawberry aldehyde. In certain embodiments, the pharmaceutical composition of the invention further comprises one or more or all of the following additional excipients: benzyl alcohol, erythrosine, and/or strawberry aldehyde.

Benzyl alcohol (phenylmethanol, CAS Registry Number [100-51-6]) may be included in the formulation as a bacteriostatic preservative (scheme 5.a). Erythrosine (disodium; 2',4',5',7'-tetraiodo-3-oxospiro[2-benzofuran-1,9'-xanthene]-3',6'-diolate, CAS Registry Entry [16423-68-0]) and strawberry aldehyde (ethyl 3-methyl-3-phenyloxirane-2-carboxylate, CAS Registry Entry [77-83-8]) may be added as a red colorant and flavour, respectively (scheme 5.b-c).

Scheme 5 A) Benzyl alcohol, B) Erythrosine, C) Strawberry aldehyde

A

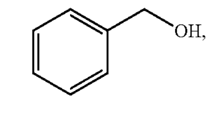

B

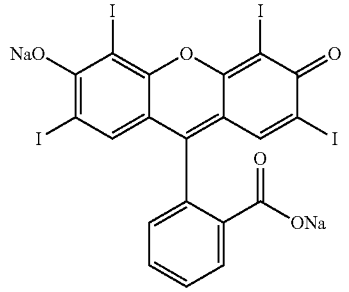

and

C

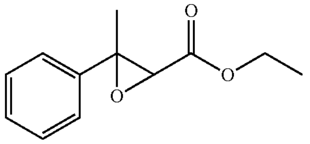

In certain embodiments, the pharmaceutical composition of the invention comprises water as a solvent, preferably as the unique solvent.

In certain embodiments, the pharmaceutical composition of the invention comprises or consist of CPX or a CPX derivate, tocofersolan (TPGS), sodium alginate, benzyl alcohol, erythrosine, strawberry aldehyde, and water.

All amounts expressed as percentages in the application refer to percentage by weight unless otherwise noted.

In certain embodiments, the composition of the invention comprises CPX or a CPX derivate such as CPX-O in an amount of 1-30% (e.g. about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30%), preferably 5-25%, more preferably 10-25% or 15-20% and even more preferably about 16.5% based on the total dry weight of the composition. In a more particular embodiment, the amount of CPX or a CPX derivative such as CPX-O is below or equal to about 21%, preferably about 20.5%, 20%, 19.5%, 19%, 18.5%, 18%, 17.5%, 17% or 16.5% or below based on the total dry weight of the composition.

The term "dry weight", as used herein, refers to the weight of a pharmaceutical composition which does not include a liquid medium or solvent. In some embodiments, the term "dry weight" refers to the weight of a pharmaceutical composition which does not include water.

In certain embodiments, the composition of the invention comprises CPX or a CPX derivate such as CPX-O in an amount of 0.1-10%, preferably 0.1-5% (e.g. about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0%), more preferably 1-4% or 1-3% and even more preferably about 2.0% based on the total weight of the composition. In a more particular embodiment, the amount of CPX or a CPX derivative such as CPX-O is below or equal to about 2.5%, preferably about 2.4%, 2.3%, 2.2%, 2.1% or 2.0% or below based on the total weight of the composition In certain embodiments, the composition of the invention comprises CPX or a CPX derivate such as CPX-O in a concentration of 1-40 mg/ml or 5-35 mg/ml, preferably 10-30 mg/ml (e.g. about 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml or 30 mg/ml), more preferably 15-25 mg/ml and even more preferably about 20 mg/ml based on the total composition. In a more particular embodiment, the concentration of CPX or a CPX derivative such as CPX-O is below or equal to about 25 mg/ml, preferably about 24 mg/ml, 23 mg/ml, 22 mg/ml, 21 mg/ml or 20 mg/ml or below based on the total composition.

In certain embodiments, the composition of the invention comprises tocopherol or a derivate thereof such as tocofersolan in an amount of 10-80%, preferably 20-70% (e.g. about 20%, 25%, 30%, 35%, 40%, 45%, 50%, 55%, 60%, 65% or 70%), more preferably 30-60% or 35-45% (e.g. about 35%, 36%, 37%, 38%, 39%, 40%, 41%, 42%, 43%, 44% or 45%) and even more preferably about 40.5% based on the total dry weight of the composition. In a more particular embodiment, the amount of tocopherol or a derivate thereof such as tocofersolan is below or equal to about 40.5%, preferably about 40%, 39.5%, 39%, 38.5%, 38%, 37.5%, 37%, 36.5%, 36%, 35.5% or 35% or below based on the total dry weight of the composition.

In certain embodiments, the composition of the invention comprises tocopherol or a derivate thereof such as tocofersolan in an amount of 0.1-10%, preferably 1-10% (e.g. about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10%), more preferably 2-8%, 3-7% or 4.5%-5.5%, and even more preferably about 4.9% based on the total weight of the composition. In a more particular embodiment, the amount of tocopherol or a derivate thereof such as tocofersolan is below or equal to about 4.9%, preferably about 4.8%, 4.7%, 4.6% 4.5%, 4.4%, 4.3%, 4.2%, 4.1% or 4.0% or below based on the total weight of the composition.

In an embodiment, the concentration of the invention comprises tocopherol or a derivate thereof such as tocofersolan in a concentration of 10-90 mg/ml (e.g. about 15 mg/ml, 20 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml or 90 mg/ml), more preferably 40-60 mg/ml and even more preferably about 50 mg/ml based on the total composition. In a more particular embodiment, the concentration of tocopherol or a derivate thereof such as tocofersolan is below or equal to about 50 mg/ml, preferably about 49 mg/ml, 48.5 mg/ml, 48 mg/ml, 47.5 mg/ml, 47 mg/ml, 46.5 mg/ml, 46 mg/ml, 45.5 mg/ml, 45 mg/ml, 44.5 mg/ml, 44 mg/ml, 43.5 mg/ml, 43 mg/ml, 42.5 mg/ml, 42 mg/ml, 41.5 mg/ml, 41 mg/ml, 40.5 mg/ml or 40 mg/ml or below based on the total composition.

In certain embodiments, the composition of the invention comprises alginate or a derivate thereof such as sodium alginate in an amount of 10-50%, preferably 20-40% (e.g. about 21%, 22%, 23%, 24%, 25%, 26%, 27%, 28%, 29%, 30%, 31%, 32%, 33%, 34%, 35%, 36%, 37%, 38%, 39% or 40%), more preferably 20-30% and even more preferably about 25% (e.g. 24.8%) based on the total dry weight of the composition. In a more particular embodiment, the amount of alginate or a derivate thereof such as sodium alginate is below or equal to about 28.9%, preferably about 28.5%, 28%, 27.5%, 27%, 26.5%, 26%, 25.5%, 25% or 24.8% or below based on the total dry weight of the composition.

In certain embodiments, the composition of the invention comprises alginate or a derivate thereof such as sodium alginate in an amount of 0.1-10%, preferably 1-8% or 1-6% (e.g. about 1.0%, 1.5%, 2.0%, 2.5%, 3.0%, 3.5%, 4%, 4.5%, 5%, 5.5% or 6%), more preferably 2-5% or 2-4% and even more preferably about 3.0% based on the total weight of the composition. In a more particular embodiment, the amount of alginate or a derivate thereof such as sodium alginate is below or equal to about 3.5%, preferably about 3.4%, 3.3%, 3.2%, 3.1% or 3.0% or below based on the total weight of the composition.

In an embodiment, the concentration of the invention comprises alginate or a derivate thereof such as sodium alginate in a concentration of 10-50 mg/ml (e.g. about 10 mg/ml, 15 mg/ml, 20 mg/ml, 25 mg/ml, 30 mg/ml, 35 mg/ml, 40 mg/ml, 45 mg/ml or 50 mg/ml), more preferably 20-40 mg/ml and even more preferably about 30 mg/ml based on the total composition. In a more particular embodiment, the concentration of alginate or a derivate thereof such as sodium alginate is below or equal to about 35 mg/ml, preferably about 34 mg/ml, 33 mg/ml, 32 mg/ml, 31 mg/ml or 30 mg/ml or below based on the total composition.

In certain embodiments, the weight ratio of CPX or a CPX derivate (e.g. CPX-O) to tocopherol or a derivate thereof (e.g. tocofersolan) is about 1:1-4, preferably about 1:1.5-3.5, more preferably about 1:2-3, still more preferably about 1:2.5.

In certain embodiments, the weight ratio of CPX or a CPX derivate (e.g. CPX-O) to alginate or a derivate thereof (e.g. sodium alginate) is about 1:0.5-2.5, preferably about 1:1-2.5, more preferably about 1:1-2, still more preferably about 1:1.5.

In certain embodiments, the weight ratio of CPX or a CPX derivate (e.g. CPX-O) to tocopherol or a derivate thereof (e.g. tocofersolan) to alginate or a derivate thereof (e.g. sodium alginate) is about 1:1-4:0.5-2.5; preferably about 1:1.5-3.5:1-2.5, more preferably about 1:2-3:1-2; still more preferably about 1:2.5:1.5.

In certain embodiments, the composition of the invention comprises a preservative such as benzyl alcohol in an amount of 1-30% (e.g. about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30%), preferably 5-25%, more preferably 10-20% or 15-20% and even more preferably about 17.4% based on the total dry weight of the composition.

In certain embodiments, the composition of the invention comprises a preservative such as benzyl alcohol in an amount of 0.1-10%, preferably 0.1-5% (e.g. about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0%), more preferably 1-4% or 1-3% and even more preferably about 2.1% based on the total weight of the composition.

In certain embodiments, the composition of the invention comprises a preservative such as benzyl alcohol in a concentration of 1-40 mg/ml or 5-35 mg/ml, preferably 10-30 mg/ml (e.g. about 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, or 30 mg/ml), more preferably 15-25 mg/ml and even more preferably about 20.9 mg/ml based on the total composition.

In certain embodiments, the composition of the invention comprises a flavour such as strawberry aldehyde in an amount of 0.1-10%, preferably 0.1-3% (e.g. about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9% or 3.0%), more preferably 0.5-2% or 0.5-1.5% and even more preferably about 0.8% based on the total dry weight of the composition.

In certain embodiments, the composition of the invention comprises a flavour such as strawberry aldehyde in an amount of 0.01-1%, preferably 0.05-0.5% (e.g. about 0.05%, 0.06%, 0.07%, 0.08%, 0.09%, 0.1%, 0.15%, 0.2%, 0.25%, 0.3%, 0.35%, 0.4%, 0.45%, 0.5%) and even more preferably about 0.1% based on the total weight of the composition.

In certain embodiments, the composition of the invention comprises a flavour such as strawberry aldehyde in a concentration of 0.1-5 mg/ml or 0.1-3 mg/ml, preferably 0.1-2 mg/ml (e.g. about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, or 2 mg/ml), more preferably about 1 mg/ml based on the total composition.

In certain embodiments, the composition of the invention comprises a colorant such as erythrosine in an amount below or equal to 1%, preferably 0.9%, 0.8%, 0.7%, 0.6%, 0.5%, 0.4%, 0.3%, 0.2%, 0.1%, 0.05%, 0.01% or below based on the total dry weight or the total weight of the composition.

In certain embodiments, the composition of the invention comprises colorant such as erythrosine in a concentration below or equal to about 1 mg/ml, preferably 0.5 mg/ml, 0.1 mg/ml, 0.05 mg/ml or below based on the total composition, more preferably about 0.028 mg/ml.

In certain embodiments, the composition of the invention comprises water in an amount of at least 50% (e.g. 55%, 60%, 65%, 70%, 75%, 80%, 85%, 90% or 95%), preferably at least 60%, 70% or 80%, more preferably 85%-95% and even more preferably about 88%.

In certain embodiments, the composition of the invention comprises water in a concentration of at least about 500 mg/ml (e.g. 555 mg/ml, 600 mg/ml, 650 mg/ml, 700 mg/ml, 750 mg/ml, 800 mg/ml, 850 mg/ml, 900 mg/ml, 950 mg/ml, 1000 mg/ml, 1050 mg/ml or 1100 mg/ml or more), preferably at least 700 mg/ml, 800 mg/ml or 900 mg/ml, more preferably 950-1050 mg/ml, and even more preferably about 1014 mg/ml.

In certain embodiments, the composition of the present invention comprises:

- 0.1-10% ciclopirox or a pharmaceutically acceptable salt, solvate or prodrug thereof (e.g. CPX-O);
- 0.1-10% tocopherol or a pharmaceutically acceptable salt, ester or ether thereof (e.g. tocofersolan); and
- 0.1-10% alginate or a pharmaceutically acceptable salt, ester or ether thereof (e.g. sodium alginate).

In certain embodiments, the composition of the present invention comprises:

- about 1-40 mg/ml ciclopirox or a pharmaceutically acceptable salt, solvate or prodrug thereof such as CPX-O,
- about 10-90 mg/ml tocopherol or a pharmaceutically acceptable salt, ester or ether thereof such as tocofersolan,
- about 10-50 mg/ml alginate or a pharmaceutically acceptable salt, ester or ether thereof such as sodium alginate,
- about 1-40 mg/ml preservative such as benzyl alcohol,
- about 0.1-5 mg/ml flavour such as strawberry aldehyde,
- ≤about 1 mg/ml colorant such as erythrosine, and water.

In certain embodiments, the composition of the present invention comprises:

- ≤about 25 mg/ml ciclopirox or a pharmaceutically acceptable salt, solvate or prodrug thereof such as CPX-O,
- ≤about 50 mg/ml tocopherol or a pharmaceutically acceptable salt, ester or ether thereof such as tocofersolan, and
- ≤about 35 mg/ml alginate or a pharmaceutically acceptable salt, ester or ether thereof such as sodium alginate.

In certain embodiments, the composition of the present invention comprises:

- ≤about 25 mg/ml ciclopirox or a pharmaceutically acceptable salt, solvate or prodrug thereof such as CPX-O,
- ≤about 50 mg/ml tocopherol or a pharmaceutically acceptable salt, ester or ether thereof such as tocofersolan,
- ≤about 35 mg/ml alginate or a pharmaceutically acceptable salt, ester or ether thereof such as sodium alginate,
- about 10-30 mg/ml preservative such as benzyl alcohol,
- about 0.1-2 mg/ml flavour such as strawberry aldehyde,
- ≤about 0.5 mg/ml colorant such as erythrosine, and water.

In certain embodiments, the composition of the present invention comprises:

- about 20 mg/ml ciclopirox olamine,
- about 50 mg/ml tocofersolan,
- about 30 mg/ml sodium alginate,
- about 20.92 mg/ml benzyl alcohol,
- about 1 mg/ml strawberry aldehyde,
- about 0.028 mg/ml erythrosine, and water.

Any or all of the above described weight or concentration embodiments of the pharmaceutical composition may be combined with each other to arrive at new embodiments. It is to be understood that the weight percentages of each component are chosen such that the total percentage does not exceed 100% with respect to the total weight of the pharmaceutical composition. In an embodiment, the weight percentages of each component are chosen such that the total percentage does not reach 100% with respect to the total weight of the pharmaceutical composition, such that further components may be present. In an embodiment, the weight percentages of each component are chosen such that the total percentage totals 100% with respect to the total weight of the pharmaceutical composition, such that further components are not present, in which case the pharmaceutical composition consists of such components.

In certain embodiments, the composition for oral administration provided in the present invention is stable at 25° C. for at least 72 days. As used herein, the term "stable", when applied to a composition in form of a solution, represents that the solution remains homogeneous (i.e. no solid and visible particles are detected) when analyzed by turbidimetric scattering, e.g. is measured using a Thermo Scientific Varioskan LUX equipment.

The composition according to the present invention may be produced according to standard procedures known to those skilled in the art. In a particular embodiment, an oral solution is prepared by dissolving the different ingredients in water, preferably under agitation. For instance, the process for preparing an oral solution may comprises the following steps: i) dissolving tocopherol or a derivate (e.g. tocofersolan) in water to form a first solution, ii) adding ciclopirox or a derivate to the first solution and dissolving it to form a second solution, iii) adding alginate or a derivate (e.g. sodium alginate) to the second solution to form a third solution, and iv) adding the remaining excipients, if any, to form the final oral solution. In a particular embodiment, the CPX derivate is CPX-O, the tocopherol derivate is tocofersolan, the alginate derivate is sodium alginate, and the remaining excipients are benzyl alcohol, strawberry flavor and erythrosine.

In another aspect, the invention refers to the pharmaceutical composition of the invention, for use as a medicament, and more specifically for use in the treatment and/or prevention of any of the diseases known to be treatable and/or preventable by ciclopirox and its derivates.

Similarly, the invention refers to the use of the pharmaceutical composition of the invention, in the manufacture of a medicament for the treatment and/or prevention of any of the diseases known to be treatable and/or preventable by ciclopirox and its derivates. Similarly, the invention refers to the pharmaceutical composition of the invention, for treating and/or preventing any of the diseases known to be treatable and/or preventable by ciclopirox and its derivates.

Similarly, the invention refers a method of treatment of a patient, notably a human, suffering a disease known to be treatable and/or preventable by ciclopirox and its derivates, or likely to suffer such a disease, which comprises administering to the patient in need of such a treatment or prophylaxis the pharmaceutical composition of the invention.

Diseases known to be treatable and/or preventable by ciclopirox and its derivates include, but are not limited to, hematologic malignancies, cancers, fungal and bacterial infections, inflammatory diseases, epilepsy and polycystic kidney disease.

Examples of hematologic malignancies under the present invention are for instance congenital erythropoietic porphyria (CEP), acute intermittent porphyria (AIP), porphyria cutanea tarda (PCT), hereditary coproporphyria (HC), harderoporphyria (HP), variegate porphyria (VP), sideroblastic anaemia (SA), erythropoietic protoporphyria and hereditary hyperbilirubinemia syndromes as well as Crigler-Najjar syndrome, Lucey-Driscoll syndrome, Gilbert syndrome, Rotor syndrome, Dubin-Johnson syndrome and other hereditary hyperbilirubinemias.

Examples of cancers under the present invention are for instance melanoma, urothelial cancer, breast intraductal carcicoma, bladder cancer and colorectal cancer.

As used herein, the terms “treat”, “treating” and “treatment” include in general the eradication, removal, reversion, alleviation, modification, or control of a disease after its onset.

As used herein, the terms “prevention”, “preventing”, “preventive”, “prevent” and “prophylaxis” refer to the capacity of a given substance, composition or medicament to avoid, minimize or difficult the onset or development of a disease before its onset.

By an “effective” amount or a “therapeutically effective amount” of a drug or pharmacologically active agent is meant a nontoxic but sufficient amount of the drug or agent to provide the desired effect. In the therapy of the present invention, an “effective amount” of ciclopirox or a pharmaceutically acceptable derivate thereof is the amount of that compound that is effective to provide the desired effect. The amount that is “effective” will vary from subject to subject, depending on the age and general condition of the individual, the particular active agent or agents, and the like. Thus, it is not always possible to specify an exact “effective amount”. However, an appropriate “effective” amount in any individual case may be determined by one of ordinary skill in the art using routine experimentation.

Generally, doses of ciclopirox or a pharmaceutically acceptable derivate thereof according to the present application for a patient, when used for the indicated effects, will range from about 0.0001 to about 100 mg per kg of body weight per day. Preferably the daily dosage will range from 0.001 to 50 mg of CPX or a derivate thereof per kg of body weight, and even more preferably from 0.01 to 20 mg or 0.01 to 10 mg of CPX or a derivate thereof per kg of body weight. However, lower or higher doses can be used, in some embodiments, the dose administered to a subject may be modified as the physiology of the subject changes due to age, disease progression, weight, or other factors.

According to an embodiment of the present invention, the compound ciclopirox or a derivate thereof is intended to modulate the heme biosynthetic pathway.

According to an embodiment of the present invention, the compound ciclopirox or a derivate thereof is intended to non-covalently associate with the heme group to stabilize it.

According to an embodiment of the present invention, the compound ciclopirox or a derivate thereof is intended to reduce the toxic porphyrin levels, in particular the levels of uroporphyrinogen (UROgenl), coproporphyrinogen I (COPROgenl) and/or their derivatives.

According to an embodiment of the present invention, the compound ciclopirox or a derivative thereof is intended to reduce the toxic levels of catabolites of the heme group, in particular the levels of bilirubin, biliverdin and/or their derivatives.

Ciclopirox can be used together with other additional useful drugs in the prevention and/or treatment of diseases. Said additional drugs can form part of the same pharmaceutical composition or, alternatively, can be provided in the form of a separated composition for their simultaneous or sequential administration to that of the pharmaceutical composition comprising ciclopirox or a derivate thereof. For example, the treatment with ciclopirox or a pharmaceutically acceptable derivate thereof could be complimented with the administration of heme derivatives or blood products to counteract the heme group deficiency or could be complimented with the administration of anti-cancer drugs to manage cancer.

The invention also refers to a combination of:

tocopherol or a pharmaceutically acceptable salt, ester or ether thereof; and alginate or a pharmaceutically acceptable salt, ester or ether thereof.

for use in decreasing or avoiding the gastrointestinal toxicity associated with oral CPX therapy. Oral CPX therapy refers to the oral administration of CPX or a derivate thereof alone or within a formulation not forming part of this invention.

In certain embodiments, GI toxicity refers to grade 1 GI toxicity. In certain embodiments, GI toxicity refers to grade 2 GI toxicity. In certain embodiments, GI toxicity refers to grade 3 GI toxicity.

Similarly, the invention refers to a method for decreasing or avoiding the gastrointestinal toxicity in a patient, notably a human, receiving or likely to receive oral CPX therapy comprising replacing that therapy for the administration of the pharmaceutical composition of the invention.

The composition according to the invention may be bioequivalent to the reference product in terms of the rate and extent of absorption, wherein the reference product is CPX or a derivate thereof alone administered orally.

Bioequivalent means that the rate and extent of absorption, that is the pharmacokinetic (PK) profile, of the composition of the invention is not significantly different from that of the reference product when they are administered at the same molar dose of the therapeutic ingredient under similar experimental conditions. As used herein, bioequivalent preferably represents that the $C_{max}$ (maximum plasma concentration) and AUC (area under the curve; drug exposure) parameters of the composition of the invention are within 80% to 125% of the corresponding parameters of the reference product for serum analysis in human subjects. The $C_{max}$ and AUC parameters may be measured with respect to CPX ($CPX_{FREE}$) and/or with respect to CPX-glucuronide ($CPX_{GLU}$).

ATL-001 Formulation

One particular example of a composition according to the present invention is the composition called ATL-001.

ATL-001, ciclopirox oral solution 20 mg/mL, is a new formulation of ciclopirox (olamine salt) for oral use, containing tocofersolan and sodium alginate, among other excipients, in an aqueous vehicle. The composition of ATL-001 is outlined in Table 1. All excipients used in ATL-001 formulation are currently on the FDA Inactive Ingredient List for Approved Drug Products. There are no additional novel excipients used.

TABLE 1

ATL-001 composition

| Substance name | Regulatory classification (Function) | Concentration (mg/ml) | % |
|---|---|---|---|
| Ciclopirox olamine | Drug Substance | 20 | 2.0 |
| Tocofersolan | Excipient (anti-GI toxicity agent) | 50 | 4.9 |
| Sodium alginate | Excipient (anti-GI toxicity agent) | 30 | 3.0 |
| Benzyl alcohol | Excipient, Preservative | 20.92 | 2.1 |
| Strawberry aldehyde | Excipient (Flavour) | 1 | 0.1 |
| Erythrosine | Excipient (Colorant) | 0.028 | 0.0 |
| Water | Solvent | 1014.12 | 88.0 |

The ATL-001 formulation avoids GI toxicity. Variants of ATL-001 formulation with higher concentrations of CPX-O have been tested for GI toxicity with favourable results. For instance, no toxicity was observed when increasing the concentration for instance to 25 mg/ml (see example 1).

Moreover, the ATL-001 formulation preserves the PK profile of the active species and preserves the PD properties, at least for the indication tested in congenital erythropoietic porphyria, demonstrating that the formulation effectively releases the active species upon gut absorption (see example 2). In contrast, the combination of CPX with only tocofersolan (without alginate) is not suitable for maintaining the PK profile observed when administered CPX alone (see example 3).

Additionally, variants of ATL-001 formulation where the concentrations of tocofersolan and alginate have been varied have been tested for thermodynamic stability (72 days). In terms of stability, the following ranges for the combination of CPX-O, tocofersolan and alginate provided excellent results: any concentration of alginate below or equal to 35 mg/mL; any concentration of tocofersolan below or equal to 50 mg/ml and any concentration of CPX-O below or equal to 25 mg/mL (see example 4).

Finally, ATL-001 complies with the required specifications by the regulatory agencies (i. e. FDA and EMA) for its use in humans. Specifically, all excipients proposed for clinical or commercial use can be obtained as compendial pharmaceutical grade. The amounts of each excipient used in the ATL-001 formulation are aligned with doses allowed for oral use as solution or other oral forms and give margins for a final ATL-001 dose administration, considering the following information from the FDA Inactive Ingredient List for Approved Drug Products: the maximum potency per unit dose currently allowed is 300 mg/mL as an oral solution for tocofersolan; for sodium alginate, maximum daily exposure is 371 mg for the oral route; for benzyl alcohol, the maximum potency per unit dose for oral solutions is 50 mg/1 ml; for the strawberry flavor is 15 mg/5 ml and for the colorant (erythrosine), maximum potency per unit dose is 0.08 mg.

Moreover, the specification for the ATL-001 formulation complies with the General Chapter: <2> ORAL DRUG PRODUCTS—PRODUCT QUALITY TESTS of the FDA guidelines. Such specifications are detailed in Table 2.

TABLE 2

ATL-001 ciclopirox oral solution specifications.

| Test parameter | Acceptance Criteria | Test Method |
|---|---|---|
| Appearance | Liquid | Visual observation: USP <631> |
| Color | Pink | Visual observation: USP <631> |
| pH | 8.8-8.9 | USP <791> |
| Identity by HPLC | Conforms (The retention time of the major peak of the assay sample corresponds to that of the standard preparation) | In-house method |
| Related substances: | | In-house method |
| Any unspecified related substance | 0.1% | |
| Total related substances | <5% | |
| Water loss | <10% | In-house method |
| Density | 1.12-1.24 | In-house method |
| Deliverable Volume | NLT 100% of liquid volume | USP <689> |
| Total Aerobic Microbial Count (CFU/g) | NMT $10^2$ | USP <1111> |

TABLE 2-continued

| ATL-001 ciclopirox oral solution specifications. | | |
|---|---|---|
| Test parameter | Acceptance Criteria | Test Method |
| Total Yeasts and Molds Count (CFU/g) | NMT 10 | USP <1111> |
| Absence of *Escherichia coli* (1 g or 1 mL) | Absence | USP <1111> |

There has been to the inventor's knowledge no disclosure of the utility of ATL-001 or any related formulation in the oral therapeutic administration of CPX or a derivative thereof such as CPX-O.

The skilled person knows that numerical values relating to measurements are subject to measurement errors which place limits on their accuracy. Where terms such as "about" or "approximately" are applied to a particular value (e.g. "about 200° C." or "approximately 200° C.") or to a range (e.g. "about x to approximately y"), the value or range is interpreted as being as accurate as the method used to measure it. Unless explicitly stated otherwise, the general convention in the scientific and technical literature may be applied so that the last digit of numerical values preferably indicates the precision of measurement. Thus, unless other error margins are given, the maximum margin is preferably ascertained by applying the rounding-off convention to the last decimal place. For instance, a value of 3.5 preferably has an error margin of 3.45 to 3.54 and a range of 2% to 10% preferably covers a range of 1.5% to 10.4%. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1% to about 5%" should be interpreted to include not only the explicitly recited values of about 1% to about 5%, but also include individual values and sub-ranges within the indicated range. Thus, included in this numerical range are individual values such as 2, 3 and 4 and sub-ranges such as from 1-3, from 2-4, and from 3-5, etc. This same principle applies to ranges reciting only one numerical value.

The following examples are provided as supporting evidence for the invention since they demonstrate that the oral pharmaceutical composition of the invention does not present any issues in terms of gastrointestinal toxicity, has a PK profile comparable to that of the active ingredient and are stable. The following examples are merely illustrative of certain embodiments of the invention and cannot be considered as restricting it in any way.

Examples

1. The Formulation of the Invention Suppresses GI Toxicity in Mice

A dose of 25 mg/kg/day of ciclopirox administered orally to mice in food pellets for 45 days (8 weeks, study TgURO_CPX37dg) is associated with gastrointestinal toxicity. Specifically, an intestinal disorder was observed, with dilation of intestinal loops due to accumulation of content and gas that affects the entire intestinal tract (FIG. 1A). Moreover, the toxicology study in rats where CPX-O was administered to rats for 4 weeks at doses of 10, 30, 100 and 300 mg/kg found gastric irritation and chronic gastritis. In this line, a Phase I study treating patients with ciclopirox olamine also showed gastrointestinal toxicity[2].

Conversely, studies assessing local tolerance of ATL-001 (administered at a dose of 25 mg/Kg of CPX FIG. 1B or 100 mg/Kg of CPX, FIG. 1C) found no signs of gastrointestinal toxicity, suggesting that this new formulation has better tolerability.

2. The Formulation of the Invention Preserves the PK Properties of CPX

Studies assessing the PK profile of ATL-001 were performed in WT mice. Comparison of the PK profile of ciclopirox formulated as ATL-001 and ciclopirox olamine (without tocofersolan and alginate) suggests that tocofersolan and alginate, at the concentrations used in ATL-001, do not significantly modify the systemic exposure to ciclopirox.

Figure 2:
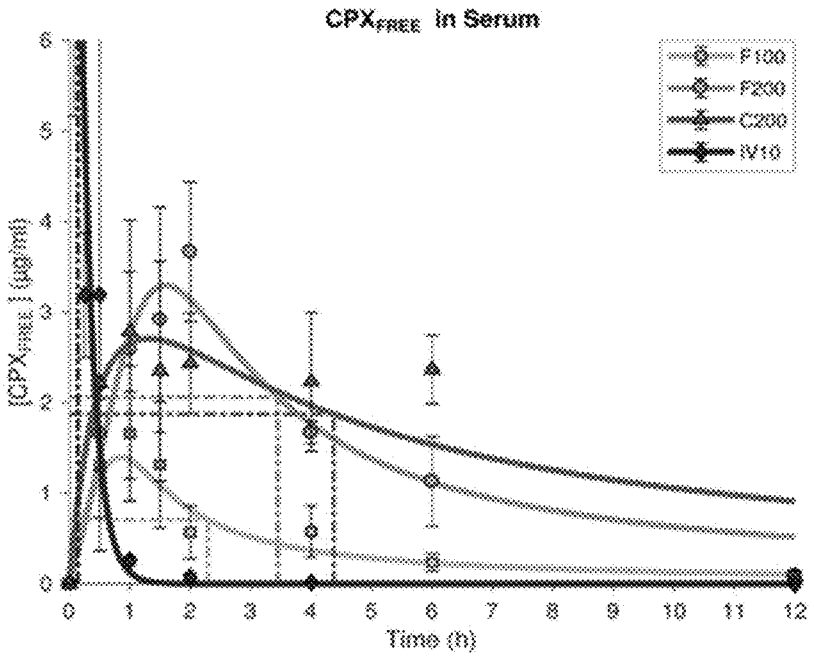
FIG. 2: Mean serum levels of ciclopirox and ciclopirox-Glu (ciclopirox glucuronide). Mice were administered 10 mg/kg of ciclopirox olamine IV (IV10), 200 mg/kg ciclopirox-olamine orally (C200), or 100 and 200 mg/kg of CPX-olamine orally formulated as ATL-001 (F100 and F200 respectively). Adjusted functions are represented with solid lines. IC50 values for each derivative is represented in dashed lines.
Figure 2:
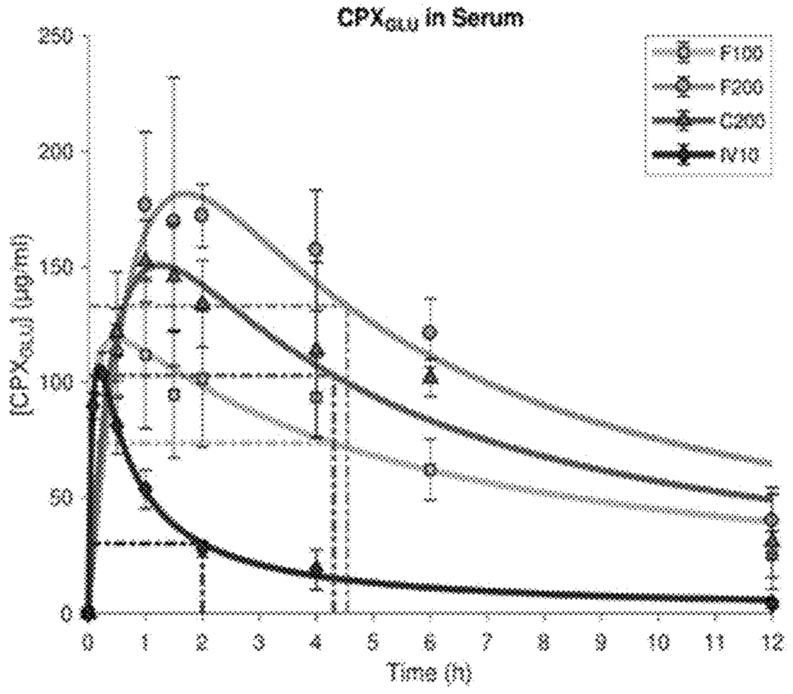

Specifically, the following groups were studied (n=3 mouse/group, FIG. 2): ciclopirox olamine 10 mg/kg administered IV (IV10), ciclopirox olamine 200 mg/kg administered orally (C200), ATL-001 corresponding to 100 mg/kg ciclopirox olamine administered orally (F100), ATL-001 corresponding to 200 mg/kg ciclopirox olamine administered orally (F200). The results of this study showed that there is a dose-dependency in the $C_{max}$ and AUC for increasing doses of ATL-001, as both AUC and $C_{max}$ for ciclopirox and ciclopirox-Glu are higher for the 200 mg/kg dose than for the 100 mg/kg dose.

Specifically, the $C_{max}$ increases from 1.4 to 3.3 µg/mL for ciclopirox and from 119.0 to 181.6 µg/mL for ciclopirox-Glu, while the AUC increases from 4.7 to 16.6 µg*h/mL for ciclopirox and from 819.7 to 1362.4 µg*h/mL for ciclopirox-Glu.

Comparison of the PK profile of 200 mg/kg of ATL-001 to 200 mg/kg of ciclopirox olamine suggests that tocofersolan and alginate, at the concentrations used, do not significantly modify the systemic exposure to ciclopirox. Also, similar PK of ciclopirox-Glu are observed for both formulations.

3. The Formulation of the Invention Preserves the PK Properties of CPX

Figure 3:
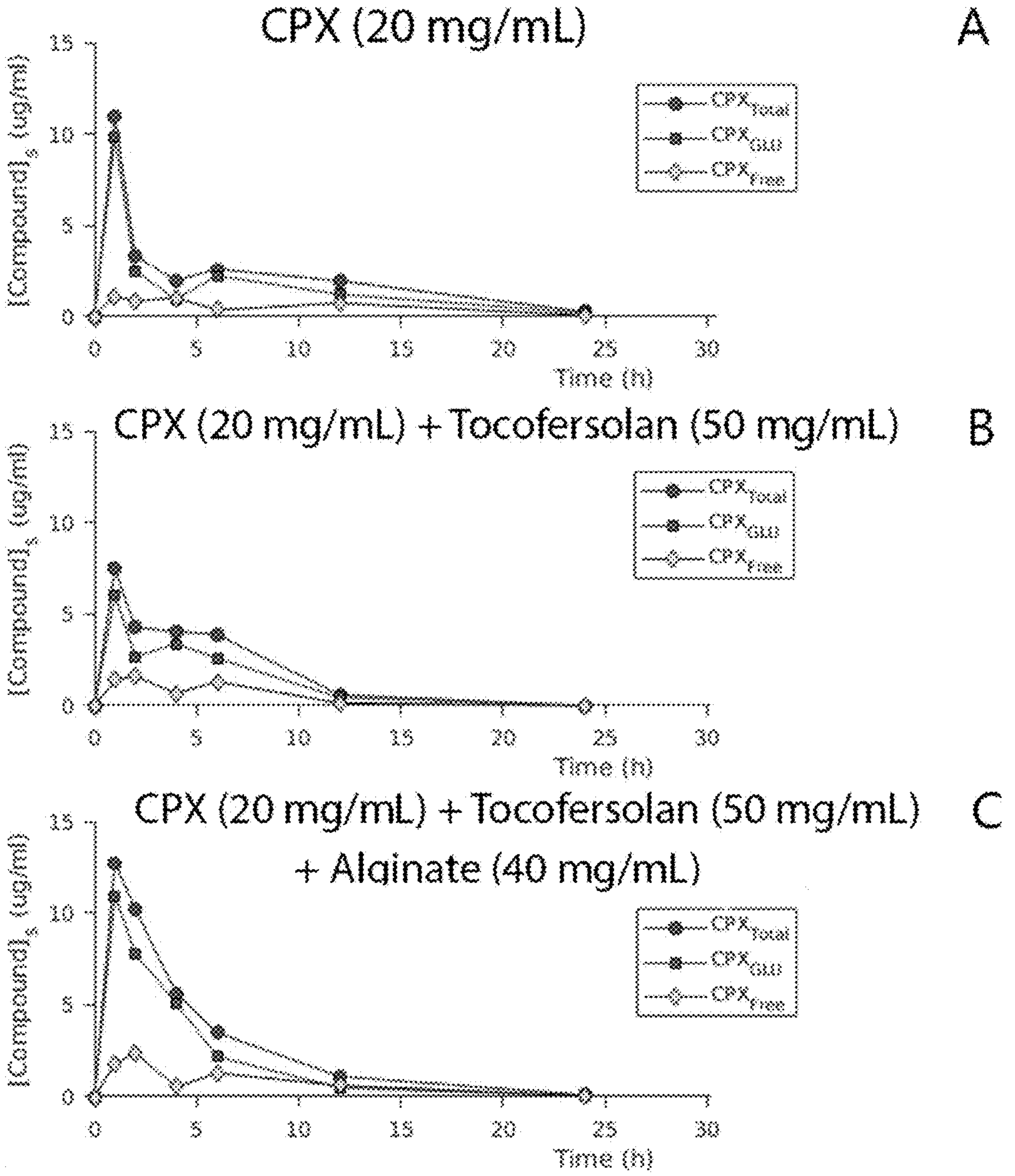
FIG. 3: Serum levels of ciclopirox, ciclopirox-Glu and ciclopirox total. Mice were administered with either CPX (A), CPX in combination with tocofersolan (B) or CPX in combination with tocofersolan and alginate (C).

This experiment explored the pharmacokinetic (PK) properties of a single dose of 25 mg/kg of CPX administered orally (20 mg/mL, dissolved in water), CPX (at 20 mg/mL in water) in combination with tocofersolan (at 50 mg/mL, dissolved in water) and CPX (at 20 mg/mL in water) in combination with tocofersolan and alginate (at 50 mg/mL and 40 mg/ml respectively, dissolved in water). For each bolus administration method 12 WT mice were used. Serum was collected after the administration at 1, 2, 4, 6, 12, 24 h. At each time point 2 mice were sacrificed. Serum samples were pooled into a single Eppendorf in each point. The results shown in FIG. 3 demonstrate that CPX in combination with tocofersolan alters the PK profile in mice, while the combination with alginate has a PK profile which is largely comparable to the one observed for CPX orally administered.

4. The Formulation of the Invention is Stable

Figure 4:
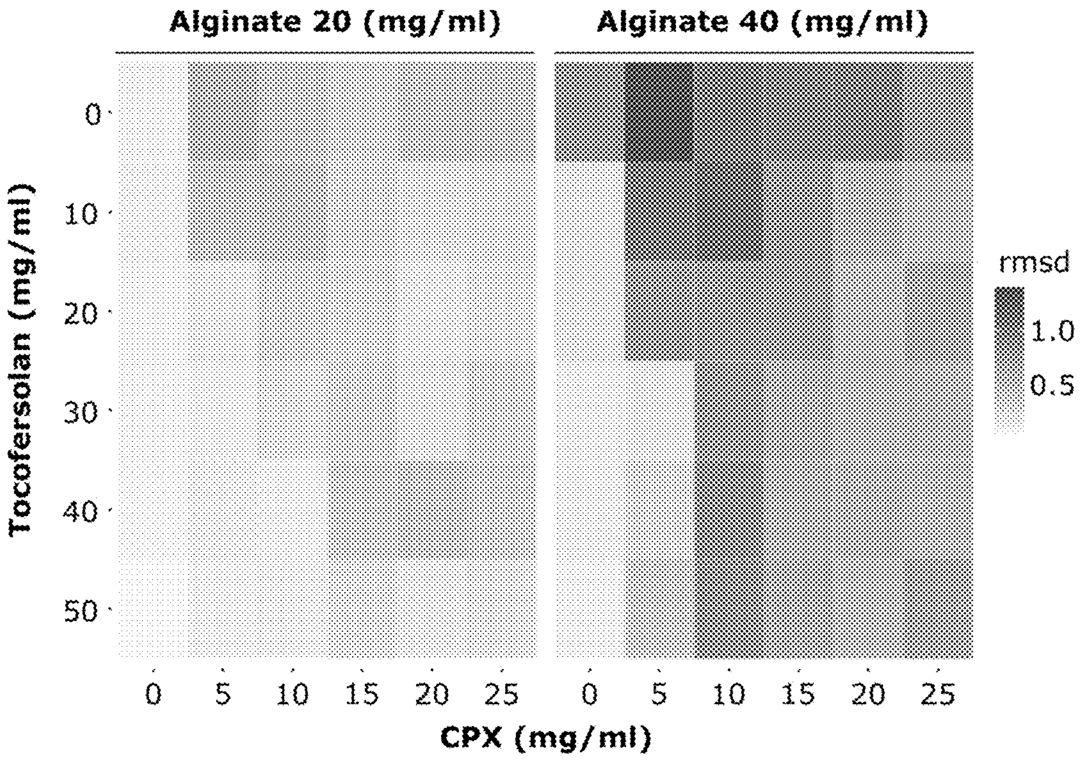
FIG. 4: Stability test for 72 days of different proportions of CPX, tocofersolan and sodium alginate. The present matrix includes the presence of benzyl alcohol, erythrosine, and strawberry aldehyde as constant co-adjuvants. Color represents the turbidimetry variability of a specific condition where red correspond to higher turbidimetry values (mixture precipitation) and yellow indicates lower opacity values.

FIG. 4 shows the combination matrix tested for 72 days of CPX, tocofersolan and alginate at different proportions. The contribution of benzyl alcohol, erythrosine, and strawberry aldehyde are neglected and kept constant. An aliquot of 1 ml of syrup was prepared for each condition in an Eppendorf. Afterwards, a 96 well-plate was loaded with 100 μl of each mixture. Internal controls were also considered in the study (not shown). The well-plate was sealed with an appropriate tape and incubated at 25° C. Turbidimetric scattering was measured using a Thermo Scientific Varioskan LUX equipment every day at 25° C. for 72 days. Turbidimetry measures the presence of solid and visible particles in a non-homogenous solution (CPX solubility). Based on these results we can conclude that the formulations comprising any concentration of alginate below or equal to 35 mg/mL, any concentration of tocofersolan below or equal to 50 mg/ml and any concentration of CPX-O below or equal to 25 mg/mL exhibit a remarkable stability for at least 72 days.

Materials and Methods

Preparation of the ATL-001 formulation. ATL-001 ciclopirox oral solution manufacturing consists of several simple dissolution steps where the different ingredients are added and dissolved in water as follows. First, tocofersolan is weight and added to approximately the 76% of water required and agitated at moderate speed until the complete dissolution of the tocofersolan. Then, ciclopirox olamine is added and agitated until complete dissolution. Subsequently, sodium alginate is added and agitated until complete dissolution. Benzyl alcohol, strawberry flavor and colorant are added in order, already pre-dissolved in a small amount of water (8%), then agitated until complete dissolution of ingredients. Finally, the primary containers are filled with the solution. Currently, up to 4 L laboratory batches have been manufactured. Variants of ATL-001 may be prepared analogously.

PK studies in mice. Serum was collected after the administration at 30 min, 1 h, 90 min, 2 h, 4 h, 6 h and 12 h for the oral administrations and at 15 min, 30 min, 1 h, 2 h, 4 h and 12 h for the IV administration. At each time point, 3 mice were sacrificed. Serum samples were pooled into a single Eppendorf for each point. Ciclopirox and its main metabolite, ciclopirox-Glu, were extracted in MeOH/H2O. K2EDTA was added to the sample to prevent ciclopirox-Fe3+ interaction. For the HPLC analysis, a C18 100×0.4 mm column was used, with a mobile phase A of formic acid 0.1%, medronic acid 10 UM in water and mobile phase B of formic acid 0.1% in acetonitrile. Peak areas were measured and the concentration of ciclopirox and ciclopirox-Glu were determined.

REFERENCES

1. Urquiza, P. et al. Repurposing ciclopirox as a pharmacological chaperone in a model of congenital erythropoietic porphyria. *Sci. Transl. Med.* 10, eaat7467 (2018). doi: 10.1126/scitranslmed.aat7467.
2. Minden, M. D. et al. Oral ciclopirox olamine displays biological activity in a phase I study in patients with advanced hematologic malignancies. *Am. J. Hematol.* 89, 363-368 (2014). doi: 10.1002/ajh.23640.
3. Weir, S. J. et al. Fosciclopirox suppresses growth of high-grade urothelial cancer by targeting the γ-secretase complex. *Cell Death Dis.* 12, (2021). doi: 10.1038/s41419-021-03836-z.
4. Weir, S. J. et al. Preclinical Pharmacokinetics of Fosciclopirox, a Novel Treatment of Urothelial Cancers, in Rats and Dogs. *J. Pharmacol. Exp. Ther.* 370, 148-159 (2019). doi: 10.1124/jpet.119.257972.
5. Al-Zubaydi, F. et al. Breast intraductal nanoformulations for treating ductal carcinoma in situ I: Exploring metal-ion complexation to slow ciclopirox release, enhance mammary persistence and efficacy. *J. Control. Release* 323, 71-82 (2020). doi: 10.1016/j.jconrel.2020.04.016.
6. Al-Zubaydi, F. et al. Breast intraductal nanoformulations for treating ductal carcinoma in situ II: Dose de-escalation using a slow releasing/slow bioconverting prodrug strategy. (2021) doi: 10.1007/s13346-021-00903-y.
7. Qi, J. et al. Ciclopirox activates PERK-dependent endoplasmic reticulum stress to drive cell death in colorectal cancer. *Cell Death Dis.* 11, 582 (2020). doi: 10.1038/s41419-020-02779-1.
8. Radadiya, P. S. et al. Ciclopirox olamine induces ferritinophagy and reduces cyst burden in polycystic kidney disease. *JCI Insight* 6, (2021). doi: 10.1172/jci.insight.141299.
9. Tanol, M. & Weir, S. J. Prodrugs of 6-cyclohexyl-1-hydroxy-4-methylpyridin-2 (1H)-one and derivates thereof. WO2012075396 A2 (7 Jun. 2012)
10. Bernardo-Seisdedos, G. et al. Improving the Pharmacological Properties of Ciclopirox for Its Use in Congenital Erythropoietic Porphyria. *J. Pers. Med.* 11, (2021). doi: 10.3390/jpm11060485
11. Lohaus, G. & Dittmar, W. Certain 1-hydroxy-2-pyridones. U.S. Pat. No. 3,883,545 (13 May 1975)
12. Stern, M. H. & Cawley J. D., M. & Weir, S. J. Water-soluble tocopherol derivatives. U.S. Pat. No. 2,680,749 (8 Jun. 1954)
13. Tavares Luiz, M. et al. The use of TPGS in drug delivery systems to overcome biological barriers. *Eur. Polym. J.* 142, 110129 (2021). doi: 10.1016/j.eurpolymj.2020.110129.
14. Severino, P. et al. Alginate Nanoparticles for Drug Delivery and Targeting. *Curr. Pharm. Des.* 25, 1312-1334 (2019). doi: 10.2174/1381612825666190425163424.
15. Builders, P. F. et al. Preparation and evaluation of mucinated sodium alginate microparticles for oral delivery of insulin. *Eur. J. Pharm. Biopharm.* 70, 777-783 (2008). doi: 10.1016/j.ejpb.2008.06.021.
16. Manabe, N. et al. Efficacy of adding sodium alginate to omeprazole in patients with nonerosive reflux disease: a randomized clinical trial. *Dis. Esophagus* 25, 373-380 (2012). doi: 10.1111/j. 1442-2050.2011.01276.x.
17. Barot, K. P. et al. Design, synthesis and docking studies of some novel (R)-2-(4'-chlorophenyl)-3-(4'-nitrophenyl)-1,2,3,5-tetrahydrobenzo[4,5]imidazo[1,2-c]pyrimidin-4-ol derivatives as antitubercular agents. *Eur. J. Med. Chem.* 83, 245-255 (2014). doi: 10.1016/j.ejmech.2014.06.019.
18. B, Z. et al. A colon targeted drug delivery system based on alginate modificated graphene oxide for colorectal liver metastasis. *Mater. Sci. Eng. C. Mater. Biol. Appl.* 79, 185-190 (2017). doi: 10.1016/j.msec.2017.05.054.
19. Pawar, S. N. & Edgar, K. J. Alginate derivatization: a review of chemistry, properties and applications. *Biomaterials* 33, 3279-305 (2012). doi: 10.1016/j.biomaterials.2012.01.007.

The invention claimed is:

1. An oral pharmaceutical composition comprising:
a therapeutically effective amount of ciclopirox or a pharmaceutically acceptable salt, solvate or prodrug thereof;
tocopherol or a pharmaceutically acceptable salt, ester or ether thereof; and
alginate or a pharmaceutically acceptable salt, ester or ether thereof.

2. The composition according to claim 1, wherein the weight ratio of ciclopirox or a pharmaceutically acceptable salt, solvate or prodrug thereof to tocopherol or a pharmaceutically acceptable salt, ester or ether thereof to alginate or a pharmaceutically acceptable salt, ester or ether thereof is 1:1-4:0.5-2.5.

3. The composition according to claim 1, comprising:
0.1-10% ciclopirox or a pharmaceutically acceptable salt, solvate or prodrug thereof;
0.1-10% tocopherol or a pharmaceutically acceptable salt, ester or ether thereof; and
0.1-10% alginate or a pharmaceutically acceptable salt, ester or ether thereof.

4. The composition according to claim 1, wherein the salt of ciclopirox is ciclopirox olamine.

5. The composition according to claim 1, wherein the tocopherol is α-, β-, γ-, or δ-tocopherol or an ester thereof selected form the group consisting of: tocopherol acetates, tocopherol propionates, tocopherol butyrates, tocopherol allophanates, tocopherol enanthates, tocopherol myristates, tocopherol palmitates, tocopherol stearates, tocopherol linoleates, tocopherol behenates, tocopherol nicotinates, tocopherol phosphates, tocopherol sulfates, tocopherol succinates, tocopherol citraconates, tocopherol α-methylcitraconates, tocopherol itaconates, tocopherol maleates, tocopherol glutaconates, tocopherol phthalates, and polyethylene glycol esters of the foregoing dicarboxylic acid esters of tocopherol.

6. The composition according to claim 1, wherein the alginate is selected from the group consisting of alginic acid, an alginate salt and an ester thereof.

7. The composition according to claim 1, further comprising a preservative, a flavour and/or a colorant.

8. The composition according to claim 7, wherein the preservative is selected from the group consisting of glycerin, potassium sorbate, sorbic acid, methyl and propylparaben, benzoic acid, sodium benzoate, benzyl alcohol and mixtures thereof.

9. The composition according to claim 7, wherein the flavour is selected from the group consisting of natural flavors extracted from plants, synthetic compounds and mixtures thereof.

10. The composition according to claim 7, wherein the colorant is selected from the group consisting of erythrosine, water soluble FD And C dyes, water insoluble FD And C dyes suspended on alumina hydrate, and colour lakes and mixtures thereof.

11. The composition according to claim 1, which comprises:
about 1-40 mg/ml ciclopirox or a pharmaceutically acceptable salt, solvate or prodrug thereof,
about 10-90 mg/ml tocopherol or a pharmaceutically acceptable salt, ester or ether thereof,
about 10-50 mg/ml alginate or a pharmaceutically acceptable salt, ester or ether thereof,
about 1-40 mg/ml preservative,
about 0.1-5 mg/ml flavour,
≤about 1 mg/ml colorant, and
water.

12. The composition according to claim 1, which comprises:
≤about 25 mg/ml ciclopirox or a pharmaceutically acceptable salt, solvate or prodrug thereof,
≤about 50 mg/ml tocopherol or a pharmaceutically acceptable salt, ester or ether thereof, and
≤about 35 mg/ml alginate or a pharmaceutically acceptable salt, ester or ether thereof.

13. The composition according to claim 1, which comprises:
about 20 mg/ml ciclopirox olamine,
about 50 mg/ml tocofersolan,
about 30 mg/ml sodium alginate,
about 20.92 mg/ml benzyl alcohol,
about 1 mg/ml strawberry aldehyde,
about 0.028 mg/ml erythrosine, and
water.

14. The composition according to claim 5, wherein the tocopherol is tocofersolan.

15. The composition according to claim 6, wherein the alginate is sodium alginate.

16. The composition according to claim 8, wherein the preservative is benzyl alcohol.

17. The composition according to claim 9, wherein the flavour is strawberry aldehyde.

18. The composition according to claim 10, wherein the colorant is erythrosine.

* * * * *